United States Patent [19]

Gerdau

[11] Patent Number: 4,966,991
[45] Date of Patent: Oct. 30, 1990

[54] PROCESS FOR THE PREPARATION OF ALKALI METAL PHOSPHONOFORMATES

[75] Inventor: Thomas Gerdau, Eppstein, Fed. Rep. of Germany

[73] Assignee: Hoechst Aktiengesellschaft, Frankfurt am Main, Fed. Rep. of Germany

[21] Appl. No.: 214,867

[22] Filed: Jul. 1, 1988

Related U.S. Application Data

[63] Continuation of Ser. No. 21,998, Mar. 5, 1987, abandoned.

[30] Foreign Application Priority Data

Mar. 7, 1986 [DE] Fed. Rep. of Germany ....... 3607445

[51] Int. Cl.$^5$ ............................................. C07F 9/38
[52] U.S. Cl. .................................................... 562/24
[58] Field of Search .................... 260/502.4 D; 562/24

[56] References Cited

U.S. PATENT DOCUMENTS 4,018,854  4/1977  McIntosh ......................... 260/502.4

FOREIGN PATENT DOCUMENTS 2435407  2/1975  Fed. Rep. of Germany .
219198  2/1985  German Democratic Rep. .
243500  3/1987  German Democratic Rep. .
541567  3/1986  Spain .
1469136  3/1977  United Kingdom .

OTHER PUBLICATIONS

Kai et al, Yiyau Gongye 1984, pp. 5-7 (translation).
Warren et al, J. Chem. Soc. (B), 1971, pp. 618-621.
Nyléen, Ber. 578: 1023–1039 (1924) translation of pertinent portions of pp. 1023–1038.
Noren, J. O. et al, Chem. Abs 98:46450y (1983).
Huang, K. et al, Chem. Abs. 101:55224k (1984).
K. Issleib et al, Phosphorus and Sulfur 30:633–636 (1987).

Primary Examiner—J. E. Evans

[57] ABSTRACT

A process for the production of alkali-phosphonoformates which comprises bringing together in a first stage a trialkyl ester of phosphonoformic acid and an aqueous solution of an alkali hydroxide at a temperature in the range from the freezing point of water and about 40° C., either keeping the resulting mixture in a second stage for further progress of the reaction and then heating the reaction mixture in a third stage to a temperature up to about 100° C. for completion of the saponification, or heating the reaction mixture immediately for completion of the saponification to a temperature of up to 100° C.

14 Claims, No Drawings

PROCESS FOR THE PREPARATION OF ALKALI METAL PHOSPHONOFORMATES

This application is a continuation of application Ser. No. 07/021,998 filed 03/05/87, now abandoned.

Phosphonoformic acid is the compound (1)

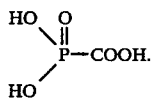
(1)

It loses $CO_2$ very easily and is therefore—at any case under normal conditions—hardly stable; phosphorous acid forms from phosphonoformic acid by means of the $CO_2$ elimination.

Various derivatives—mainly some esters and salts—of phosphonoformic acid are known as plant growth-regulating substances (cf. British Patent Specification No. 1469136) and substances with an antiviral action—for example against herpes viruses (cf., for example, DD-A-219,198).

The esters of phosphonoformic acid—such as the triethyl ester—can be prepared by Arbusow reaction of esters of phosphorous acid with chloroformates (P. Nylen, Ber. 57 (1924), pp. 1023–1038, particularly p. 1027 and 1035). In the case of the preparation of triethyl ester, the corresponding reaction equation is as follows:

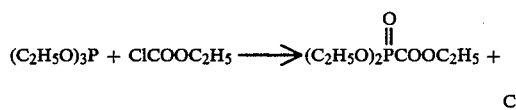

According to p. 1028 of the abovementioned article by P. Nylen, triethyl phosphonoformate is quantitatively cleaved into phosphorous acid and $CO_2$ (and probably also ethanol) on boiling with water or acids.

The trisodium salt of phosphonoformic acid is produced on alkaline saponification using sodium hydroxide solution—according to pages 1029 and 1036 of this article.

Apart from the fact that the saponification is or was carried out by refluxing for 3 to 4 hours, a more exact procedure for carrying out the alkaline saponification is not given; nor is a corresponding mention of yields apparent from the literature citation.

However, according to Example 1 of U.S. Pat. No. 4,018,854, issued to McIntosh, and Example 1 of corresponding. British Patent Specification No. 1469136, a yield (calculated from the communicated data) of only 15.7% of trisodium phosphonoformate (as the hexahydrate) was obtained by refluxing triethyl phosphonoformate with aqueous sodium hydroxide solution for 2 hours "by the Nylen process" (ibid). The low yield is obviously caused by the fact that the triesters of phosphonoformic acid are sensitive to cleavage (into phosphite and $CO_2$).

S. Warren and M. R. Williams (J. Chem. Soc. (B), 1971, pp. 618–621) obtained an only slightly higher yield of the corresponding trisodium phosphonoformate (19%) on alkaline saponification of triethyl phosphonoformate using aqueous sodium hydroxide solution. The saponification was carried out here by adding aqueous sodium hydroxide solution to the triethyl phosphonoformate, cooling not being effected. The batch was heated as a result of the heat of saponification; the ethanol liberated was removed by distillation.

In Yiyao Gongye 1984, (3), pp. 5–7, though, Huang Kai and Wang Bijun report a yield of 46% of trisodium phosphonoformate on alkaline saponification of triethyl phosphonoformate using aqueous sodium hydroxide solution. According to the final paragraph on page 6, 82.5 ml of 40% strength sodium hydroxide solution were added, with stirring, to 34.7 g of triethyl phosphonoformate, and the mixture was heated for half an hour. After cooling and filtering off under suction, 16 g of trisodium phosphonoformate (as the hexahydrate) were obtained; a further 6.8 g were obtained from the mother liquor.

A still higher yield of trisodium phosphonoformate—namely 64%—was obtained in Example 7 of the DD-A-219,198 mentioned initially—not however, on alkaline saponification of triethyl phosphonoformate, but instead of bis-trimethylsilyl ethoxycarbonyl phosphonate

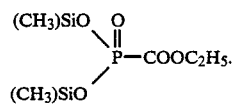

In the example mentioned, mention is even made of a 100% yield; however, a yield of only 64% is clearly calculated from the data communicated.

Although the known processes for the preparation of alkali metal phosphonoformates by alkaline saponification of phosphonoformates are simple to carry out and start from simple and easily accessible starting materials, a yield of greater than 50% of theory is only achieved in one single case. This case in which a higher yield is achieved (DD-A-219,198—64%) requires the employment of the not entirely easily accessible bis-trimethylsilyl alkoxycarbonyl phosphonate as starting material.

It was therefore desirable, and the object was, to improve the known processes for the preparation of alkali metal phosphonoformates or to provide a new, improved and more economic process.

According to the invention, it was possible to achieve this object by means of a two-stage procedure of alkaline saponification of trialkyl phosphonoformates, care being taken, in particular, that the temperature at the start of the saponification reaction—in the first process stage—remains relatively low.

The invention relates to a process for the preparation of alkali metal phosphonoformates by alkaline saponification of trialkyl phosphonoformates using an aqueous alkali metal hydroxide solution, which comprises (a) keeping the temperature of the reaction mixture between the freezing point of water and about 40° C., preferably not allowing it to increase above about 30° C., and, if appropriate, keeping it in this temperature range for some time, during the mixing of the trialkyl phosphonoformate and the aqueous alkali metal hydroxide solution, and which comprises (b) subsequently heating the reaction mixture at temperatures up to about 100° C. until the saponification is complete.

The alkaline saponification of the phosphonoformate is an exothermic reaction. Since the major part of the saponification proceeds immediately after contact of the ester with the alkali metal hydroxide solution, the reaction mixture warms fairly quickly and intensively when the mixing of the reactants is not too slow. In order that the temperature limits of stage (a) of the process according to the invention are not exceeded, it is therefore normally necessary to cool the reaction mixture here. The temperature range of stage (a) is defined at its lower limit the freezing point of water, so that approximately 0° C. can be specified as the lower temperature limit; a more favorable temperature range is between about 15° and 30° C.

No particular heat of reaction is produced when the mixing of the reactants is complete, so that the cooling can then, if appropriate, be removed. It is expedient to then keep the reaction mixture within the temperature range of stage (a) for some time, which can be achieved by allowing to stand or stirring at room temperature.

In order to complete the saponification, the mixture is then heated to temperatures up to about 100° C., advantageously to temperatures between about 80° and 100° C., which can expediently be carried out under reflux and, if appropriate, with intensive mixing, for example by stirring. The completion of the saponification can be followed, if appropriate, by taking appropriate samples from the reaction mixture. The saponification is normally complete when both of the two stages (a) and (b) are allowed to proceed for about 0.5 to 2 hours.

Yields of the desired alkali metal phosphonoformates of greater than 80% of theory are usually obtained by this procedure. It is extremely surprising that the result is improved by such a jump due to the simple modification, according to the invention, of the known saponification process (keeping the temperature low at the beginning of the saponification).

The starting compounds for the process according to the invention are trialkyl phosphonoformates of the formula

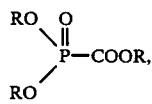

in which the radicals R, independently of one another, represent alkyl radicals. The length of the alkyl radical is, in principle, unimportant. $C_1$-$C_4$-alkyl radicals, particularly $CH_3$ or $C_2H_5$, are preferred. Examples of such esters are the trimethyl, triethyl, the various tripropyl and tributyl esters, such as the tri-n-propyl and tri-n-butyl esters, and the coesters

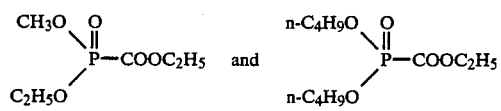

The compounds can be obtained in a known fashion, for example by Arbusow reaction of the appropriate trialkyl phosphites and alkyl chloroformates.

Suitable aqueous alkali metal hydroxide solutions are, in principle, the aqueous solutions of all alkali metal hydroxides (LiOH, NaOH, KOH, RbOH and CsOH); the aqueous NaOH and KOH solutions are preferred.

The concentration of the aqueous alkali metal hydroxide solution may be in a broad range. Approximately 15 to 50% strength (by weight), particularly approximately 20 to 30% strength (by weight) solutions are preferred.

The reaction equation on which the saponification reaction is based is:

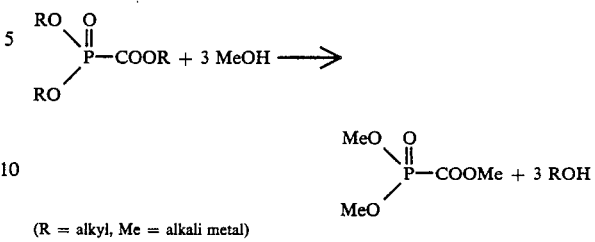

(R = alkyl, Me = alkali metal)

According to the stoichiometry of this reaction, 3 moles of alkali metal hydroxide are necessary for the saponification of one mole of trialkyl phosphonoformate. Accordingly, the trialkyl phosphonoformate and alkali metal hydroxide reactants are also employed in the molar ratio 1: at least approximately 3. A ratio of 1: approximately 5 to 6 is preferred.

The process is expediently carried out by initially introducing the aqueous alkali metal hydroxide solution and adding the trialkyl phosphonoformate (if appropriate with stirring) dropwise with cooling to the former. It should be ensured here that the temperature of the reaction mixture does not exceed the upper limit (about 40° C., preferably only about 30° C.) specified for reaction stage (a). When the addition of the trialkyl phosphonoformate is complete, the cooling can normally be removed without the temperature increasing significantly. Stirring for approximately a further 0.5 to 1 hour at room temperature is advantageous. The further stirring is part of process stage (a).

Of course, it is, in principle, also possible to initially introduce the trialkyl phosphonoformate and to meter in the aqueous alkali metal hydroxide solution, or to meter the trialkyl phosphonoformate and the aqueous alkali metal hydroxide solution simultaneously into an appropriate reaction vessel, just as long as the temperature conditions according to the invention are observed. When the reaction is complete, the batch is allowed to cool and crystallize out, and work-up is effected in a conventional fashion.

In a preferred embodiment of the process, the appropriate starting trialkyl phosphonoformate is employed directly for the alkaline saponification in the form of the crude reaction mixture from the Arbusow reaction of trialkyl phosphite and alkyl chloroformate.

The alkali metal phosphonoformates obtained in high yield and purity by the process according to the invention can be converted, if desired, in a conventional fashion into other salts of phosphonoformic acid—for example the ammonium and alkyl ammonium, alkaline earth metal, Zn and/or Mn salts; this can be carried out, for example, by passing an aqueous solution of the alkali metal phosphonoformate through an ion exchanger column which is charged with other appropriate cations.

The following examples are intended to describe the invention in greater detail.

EXAMPLE 1

Trisodium phosphonoformate hexahydrate (a) 120 g (3 mol) of sodium hydroxide were dissolved in 350 ml of water, and 105 g (0.5 mol) of triethyl phosphonoformate were added dropwise within 30 minutes. The internal temperature was kept at 20°–25° C.

by cooling using an ice bath. When the addition was complete, the ice bath was removed and the reaction mixture was stirred for 1 hour at room temperature.

(b) The mixture was subsequently refluxed for 1 hour and kept at 0° C. for 24 hours for completion of the crystallization. After filtering off the crystals under suction and drying in a vacuum desiccater, 125.5 g of a 99.5% pure product ($^{31}$P NMR), which corresponds to a yield of 84% of theory were obtained. After recrystallization from 400 ml of water, 122.0 g were recovered in the form of well-formed crystals, which were 99.9% pure.

$Na_3CO_5P.6H_2O$ MW 300.04 $^{31}$P NMR 0.8 ppm.

EXAMPLE 2

Trisodium phosphonoformate hexahydrate and pentahydrate 83.1 g (0.5 mol) of triethyl phosphite were warmed to 60° C., 56.7 g (0.6 mol) of methyl chloroformate were added dropwise within 1 hour, and the mixture was warmed at 100° C. for 15 minutes when the addition was complete. The amount of ethyl chloride collected in a cold trap was 33.2 g.

(a) The reaction solution was then added dropwise, within 45 minutes, to a solution, cooled using ice, of 100 g (2.5 mol) of sodium hydroxide in 300 ml of water, the internal temperature not increasing above 25° C. When the addition was complete, the mixture was stirred for 1 hour at room temperature and (b) subsequently refluxed for 1 hour. After complete crystallization, 121 g of trisodium phosphonoformate hexahydrate, which was 99% pure (31P NMR), were obtained. This corresponds to a yield of 80% of theory.

After storing in a drying cabinet (50° C., 200 mbar) for 4 hours, 113.7 g of the corresponding pentahydrate were obtained.

$Na_3CO_5P.5H_2O$ Calc.: Na 24.4%; C 4.3%; H 3.6%; P 11.0%;

MW 282.01; Found: Na 24.5%; C 4.6%; H 3.5%; P 11.2%.

EXAMPLE 3

Tripotassium phosphonoformate (a) 52.5 g (0.25 mol) of triethyl phosphonoformate were added dropwise, within 30 minutes to a solution of 84.2 g (1.5 mol) of potassium hydroxide in 175 ml of water, and an increase of the internal temperature above 25° C. was prevented by cooling using an ice bath. The mixture was subsequently stirred for 30 minutes at room temperature and (b) refluxed for 1 hour. The reaction solution was evaporated to dryness, and 51.7 g of tripotassium phosphonoformate were obtained from the residue by recrystallization. The residue contained about 5% potassium phosphite. This corresponds to a yield of 86% of theory.

$K_3CO_5P$ MW 240.29; Calc.; K 48.8%; C 5.0%; P 12.9%;

Found: K 49.5%; C 5.4%; P 12.5%.

I claim:

1. A process for the production of alkali-phosphonoformates which comprises reacting in a first stage a trialkyl ester of phosphonoformic acid with an aqueous solution of an alkali hydroxide, the temperature being kept in the range of from the freezing point of water to 40° C., to effect partial saponification of the ester bonds, thus suppressing decarboxylation, then either keeping the resulting mixture in a second stage in the said temperature range for further progress of the reaction and then heating the reaction mixture in a third stage to a temperature above about 40° C. and up to 100° C. for completion of the saponification, or heating the reaction mixture in a second stage immediately for completion of the saponification to a temperature above 40° C. and up to 100° C.

2. A process as claimed in claim 1, wherein the first and latest stage are each conducted for a period in the range of from 0.5 to 2 hours.

3. A process as claimed in claim 1 wherein the trialkyl ester of phosphonoformic acid is applied in the form of a crude reaction product as obtained by the reaction of trialkylphosphite and chloroformic alkyl ester according to the Arbusow-reaction.

4. A process as claimed in claim 1, wherein the first stage is carried out at a temperature in the range of from 0° C. to 40° C. and the trialkyl phosphonoformate and alkali metal hydroxide are employed in a molar ratio of about 1:3 to about 1:6.

5. A process as claimed in claim 4, wherein the first stage is carried out at a temperature in the range of from about 15° to about 30° C.

6. A process as claimed in claim 1, wherein the last stage is carried out at a temperature in the range of from about 80° to 100° C.

7. A process as claimed in claim 5 wherein the last stage is carried out at a temperature in the range from about 80° to 100° C.

8. A process as claimed in claim 1, wherein the trialkyl ester of phosphonoformic acid is derived from alkyl each having from 1 to 4 carbon atoms.

9. A process as claimed in claim 1, wherein the trialkyl ester of phosphonoformic acid is derived from alkyl each having from 1 to 2 carbon atoms.

10. A process for the production of an alkali metal phosphonoformate by saponification which comprises:
    in a first stage, providing an aqueous reaction mixture containing a trialkyl ester of phosphonoformic acid and at least three moles, per mole of said trialkyl ester, of alkali metal hydroxide, and maintaining said reaction mixture at a temperature 0° C. which is less than 40° C. to effect partial saponification of the ester bonds, thus suppressing decarboxylation;
    then in a subsequent stage, heating the reaction mixture to an elevated temperature above 40° C., but not exceeding about 100° C. until the saponification is complete; and
    recovering the alkali metal phosphonoformate product from the reaction mixture.

11. A process as claimed in claim 10, wherein, subsequent to said first stage, the resulting mixture is kept in a second stage at a temperature between 0° and 40° C. for further progress of the reaction, and the resulting mixture is then heated in a third stage to said elevated temperature for completion of the saponification.

12. A process as claimed in claim 10, wherein, subsequent to said first stage, the resulting mixture is heated substantially immediately to a said elevated temperature for completion of the saponification.

13. A process for the production of alkali-phosphonoformates which comprises reacting in a first stage a trialkyl ester of phosphonoformic acid with an aqueous solution of an alkali hydroxide, the temperature being kept in the range of from the freezing point of water to 40° C., to effect partial saponification of the ester bonds, thus suppressing decarboxylation, then either keeping the resulting mixture in a second stage in the said temperature range for further progress of the reaction and then heating the reaction mixture in a third stage to a temperature in the range of from 80° C. to 100° C. for completion of the saponification, or heating the reaction mixture in a second stage immediately for completion of the saponification to a temperature in the range of from 80° C. to 100° C.

14. In a process for the production of alkali-phosphonoformates by reacting a trialkyl ester of phosphonoformic acid with an aqueous solution of an alkali hydroxide at a temperature in the range from ambient temperature to boiling temperature to effect saponification of the ester bonds, the improvement which comprises carrying out the reaction in steps such that in the first stage it is kept in the range of from the freezing point of water to 40° C., by cooling the aqueous solution of alkali hydroxide, to effect partial saponification of the ester bonds, thus suppressing decarboxylation, then either keeping the resulting mixture in a second stage in the said temperature range for further progress in the reaction and then heating the reaction mixture in a third stage to a temperature above 40° C. and up to 100° C. for completion of the saponification, or heating the reaction mixture in a second stage immediately for completion of the saponification to a temperature above 40° C. and up to 100° C.

* * * * *

UNITED STATES PATENT AND TRADEMARK OFFICE
CERTIFICATE OF CORRECTION

PATENT NO.   :   4,966,991
DATED        :   October 30, 1990
INVENTOR(S)  :   Thomas Gerdau It is certified that error appears in the above-identified patent and that said Letters Patent is hereby corrected as shown below:

In claim 10, column 6, line 44, before "0°C", please insert -->--.

Signed and Sealed this

Tenth Day of March, 1992

*Attest:*

HARRY F. MANBECK, JR.

*Attesting Officer*     *Commissioner of Patents and Trademarks*